United States Patent [19]

Lyttle

[11] Patent Number: 5,688,940
[45] Date of Patent: Nov. 18, 1997

[54] LINKER FOR IMMOBILIZATION, MODIFICATION AND SUBSEQUENT RELEASE OF OLIGOMERS WITH A TERMINAL HYDROXYL GROUP

[75] Inventor: Matthew H. Lyttle, Marin, Calif.

[73] Assignee: Biosearch Technologies, Inc., San Rafael, Calif.

[21] Appl. No.: 595,104

[22] Filed: Feb. 1, 1996

[51] Int. Cl.⁶ .......................... C07H 21/00; C07H 21/02; C07H 21/04

[52] U.S. Cl. .................. 536/25.3; 536/25.33; 536/25.34; 435/91; 435/92

[58] Field of Search ............................. 536/23.1, 24.3, 536/25.3, 25.33, 25.34; 435/91, 92

[56] References Cited

U.S. PATENT DOCUMENTS

| | | | |
|---|---|---|---|
| 5,414,077 | 5/1995 | Lin et al. | 536/24.3 |
| 5,539,097 | 7/1996 | Arnold | 536/25.3 |

OTHER PUBLICATIONS

S.L. Beaucage and R.P. Iyer, Advances in the Synthesis of oligonucleotides by the Phosphoramidite Approach, Tetrahedron, vol. 48, pp. 2223–2311, 1992.

H. Koster and K. Heyns, Polymer Support Oligonucleotide Synthesis. VII Use of Sephadex LH 20. Tetrahedron Letters, pp.1531, 1972.

G. R. Gough, M.J. Brunden and P.T. Gilham, 2'(3')–O–Benzyoyluridine 5' Linked to Glass: An All–purpose Support for Solid Phase Synthesis of Oligodeoxyribonucleotide, Tetrahedron Letters, vol. 24, pp. 5321–5324, 1983.

R. Crea and T. Horn, Synthesis of Oligonucleotides on Cellulose by a Phosphotriester Method, Nucleic Acids Researchh, vol. 8, pp. 2331–2348, 1980.

S. Scott, P. Hardy, R.C. Sheppard and M.J. McLean, A Universal Support for Oligonucleotide Synthesis, in "Innovations and Perspectives in Solid–Phase Synthesis", R. Epton, Ed., Mayflower Publishers, pp. 115–124, 1994.

P.S. Nelson, R.A Frye and E. Liu, Bifunctional Oligonucleotide Probes Synthesized Using a Novel CPG Support Are Able To Detect Single Base Pair Mutations, Nucleic Acids Research, vol. 17, pp. 7187–7194, 1989.

H. Vu, N. Joyce, M. Rieger, D. Walker, I. Goldknopf, T.S. Hill, K. Jayaraman and D. Mulvey, Use of Phthaloyl Protecting group for the Automated Synthesis of 3'–[(Hydroxypropyl)amino] and 3'–[(Hydroxylpropyl)triglycyl] Oligonucleotide Conjugates, Bioconjugate Chem., vol. 6, pp. 599–607 (1995).

S.L. Beaucage and M.H. Caruthers, Deoxynucleoside Phosphoramidites—A New Class of Key Intermediates for Deoxypolynucleotide Synthesis, Tetrahedron Letters, vol. 22, pp. 1859–1862, 1982.

Y. Hayakawa, S. Wakabayashi, H. Kato and R. Noyori, The Allylic Protection Method in Solid–Phase Oligonucleotide Syntesis. An Efficient Preparation of Solid–Anchored DNA oligomers, J. Amer. Chem. Soc., vol. 112, pp. 1691–1696., 1990.

D. Hudson and M.H. Lyttle, Allyl Based Side–Chain Protection for SPPS, inPeptides, Chemsitry and Biology, Proceedings of the Twelfth American peptide Society, J. Rivier and J.A. Smth, Eds., pp. 583–584 (1992).

Ikehara et al., "The Synthesis of Polynucleotides," *Advances in Carbohydrate Chemistry and Biochemistry*, 36, 135–213 (1979); only pp. 135 and 207–213 supplied.

*Primary Examiner*—John Kight
*Assistant Examiner*—L. Eric Crane

[57] ABSTRACT

The invention is a method which allows the attachment of an alcohol to a substrate by the use of which chemical and/or enzymatic transformations of the alcohol are facilitated, and subsequently the modified alcohol can be released, if desired, under exquistely mild conditions, after selective removal of a protecting group from an expulsion promoting amino group.

15 Claims, 1 Drawing Sheet

LINKER FOR IMMOBILIZATION, MODIFICATION AND SUBSEQUENT RELEASE OF OLIGOMERS WITH A TERMINAL HYDROXYL GROUP

BACKGROUND

1. Field of the Invention

Hydroxylic compounds are ubiquitous in nature; including steroids, sugars, amino acids (and peptides and proteins derived from them), DNA and RNA. The invention represents a unique method for the immobilization of hydroxylic compounds, providing, additionally, a mild, specific means to liberate into solution the compound, or derivatives of the compound formed by chemical or enzymatic processing. This process is termed amine (or anchiomeric) promoted expulsion (APEX).

The field of the invention includes diagnostic, separations and synthetic applications. Immobilized enzymes, antibodies and nucleic acids are useful in the diagnosis of disease states. Immobilized peptides, DNA, steroids, chiral molecules, drug and dye derivatives are useful for analytical and preparative separations of biologically important compounds. Immobilized chemical compounds may be chemically and enzymatically modified to generate novel synthetic variations useful for research and pharmaceutical applications.

2. Prior Art

No method has been previously described which allows the rapid localization of hydroxylic compounds, the application of a diverse set of chemical or enzymatic modifications, and the subsequent release under very mild conditions. That such a method is highly desirable can be seen from the continuing quest in the literature for such a "universal" support, and the obvious short-comings of the procedures which have been developed.

Several methods are available for hydroxyl immobilization, and cleavage into strongly basic solution. The preeminent method, the formation of the hemi-succinate derivative, coupling to the support, and cleavage with conc. ammonia is well known (for a review see S. L. Beaucage and R. P. Iyer, Tetrahedron, 1992, 48, 2223). Methods to overcome this tedious and destructive protocol all utilize uridine derivatives, in one form or another (H. Koster and K. Heyns, Tetrahedron Letters, 1972, 1531; G. R Gough, M. J. Brunden and P. T. Gilham, Tetrahedron Letters, 1981, 22, 4177, R. Crea and T. Horn, Nucleic Acids Research 1980, 8, 2331). Basically, the approaches entail the attachment of 2' or 3' benzoate derivatives of uridine to the solid support. The unprotected 2' or 3'hydroxyl serves as the assembly point for the oligonucleotide, after synthesis treatment under drastic base conditions (16 hours at 55° C. in conc. ammonia, removes the benzoyl protection, and the liberated hydroxyl can then attack the adjacent phosphate, forming a pyrophosphate with expulsion of the desired nucleotide. A recent variation used a related cyclic diol, rather than uridine (S. Scott, R. C. Sheppard and M. J. McLean, in "Innovations and Perspectives in Solid Phase Synthesis, R. Epton, Ed., Mayflower Publishers, p.115, 1994) but still many hours of treatment at 60° are required. Not only are the conditions too drastic, but the economical viability of the method is unsure because of the high expense of the materials and manipulations required.

This invention starts with the description by Nelson of a method to prepare modified DNA containing a pendant 3' amino group, which renders it resistant to metabolic digestion, and allows 3' labelling to be performed (P. S. Nelson, R. A. Frye and E. Lieu, Nucleic Acids Research, 1989, 17, 7187). Subsequently, Vu observed that when Fmoc was used to protect the pendant amino group, that some formation of unmodified nucleotide resulted (H. Vu, N. Joyce, M. Rieger, D, Walker, I. Goldknopf, T. S. Hill, K. Jayaraman and D. Mulvey, Bioconjugate Chem., 1995, 6, 599). By screening of different protecting groups removable under more forcing conditions, finally electing for the phthaloyl group, they were able to eliminate this side-reaction. This invention provides allyloxycarbonyl, and related protection, removable under mild conditions, wherebye the phosphate triester protection is not affected. A subsequent intramolecular attack of the amino group then occurs under mild aqueous buffered conditions liberating the hydroxylic compound. The mildness of these conditions allow the incorporation of sensitive dyes into the molecules, as well as providing a method to cleave molecules bearing pendant protecting groups, even phosphate triesters, such blocked derivatives being useful for further reactions.

The selection of allyloxycarbonyl is well established in a variety of applications where specific removal is advantageous, reference is given to a patent in French (Loffet and Zhang, WO 92/19643) which describes application to side-chain protection in peptide synthesis, as well as to the seminal original contribution in this area by this inventor (Hudson and Lyttle, 1992).

OBJECTS AND ADVANTAGES OF THE INVENTION

The prior art teaches the usefulness of a universal support, and the need for a method which provides a mild liberation of hydroxylic native or modified compound into solution. The studies of Nelson and Vu, already referenced, describe compounds related to those of this invention, but do not teach the usefulness for hydroxyl regeneration when an appropriately positioned amino group is deprotected spatially adjacent to a protected phosphate triester. Several objects and advantages of the invention are described in the following section.

It is an object of the invention to provide a method to immobilize or otherwise restrain hydroxylic compounds, to subsequently subject them to optional chemical or enzymatic modification steps, to remove a protectiong group on a proximal amino group under mild conditions which do not effect phosphate triester protecting groups, and to treat the deprotected material under mild conditions eliminating or expelling the hydroxylic or modified hydroxylic compound.

It is a further object of the invention to provide a method suitable for the synthesis of any desired oligonucleotide (DNA or RNA), synthesized in a step wise or block wise manner from either the 3' terminus or the 5' terminus, starting from just one linker functionalized support material.

It is a further object of this invention to provide a method. wherebye the immobilization of a hydroxylic phosphoramidite derivative can be performed automatically using standard programming. This ability is a primary advantage of the method. A further advantage of the method is the mildness of the deproetction and cleavage steps, far milder than any other described linker. A further advantage of the method is that a two step process is involved, firstly deprotection of the proximal amino group, followed by intramolecular cyclization and expulsion of the desired material. This simple process allows washing to totally remove all reagents and byproducts from the amine deprotection step, their residues therefore do not contaminate the product, as would be the case for a single step process.

It is also an advantage of the preferred form of the invention, which utilizes 3-amiopropane-1,2-diol as a starting material for APEX linker construction, that this material is readily available in high purity, and economically. This attribute makes the APEX methodology viable commercially, and of especial interest in large scale production of organic hydroxylic compounds by solid-phase synthesis.

It is an object of the invention to provide a method suitable for combinatorial chemistry. A principal advantage of the method is that after transformation of R to R*, the alcohol is regenerated in exactly the same state as it originated, and bears no vestage of the immobilization chemistry. The method is, therefore, especially useful in pharmaceutical development, wherebye a single alcohol could be treated with a variety of reagents, either separately or in mixtures, and each product or pool taken on to further series of transformations, therebye generating large numbers of compounds for evaluation.

A further advantage of the invention is that it provides a linker for attachment of the key functionalities to any chemically derivatized surface or particle, making its application very general, rather than limiting it to any specific support type.

Figure 1:
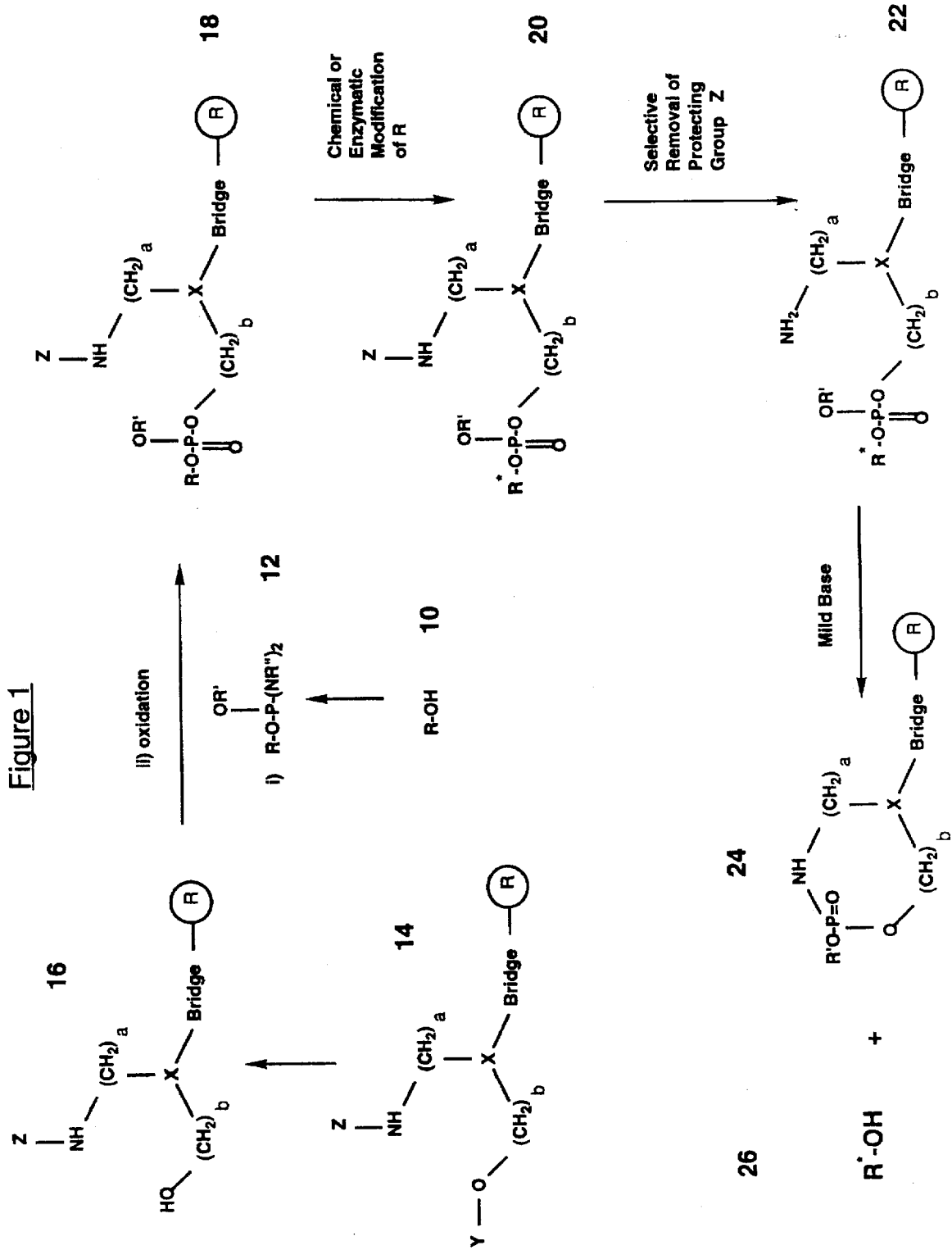
FIG. 1 schematically outlines the steps involved in the invention, the transformation of alcohol R—OH (10) to R*—OH (26). The alcohol is converted to its phosphoramidite derivative (12), which is coupled to the hydroxyl of the linker functionalized substrate (16); which is in turn derived from a protected precursor (14). After coupling the phosphite triester bond is oxidized to the corresponding phosphate triester (18). The substrate bound alcohol R—OH is then transformed to R*—OH (20). Selective removal of the pendant amino protecting group Z gives the deprotected form (22). A final mild base promoted elimination of the product R*—OH (26) occurs leaving a cyclic phosphoramidate (24) on the substrate.

Reference Numerals
10 A hydroxylic compound, R—OH.
12 A phosphoramidite derivative of R—OH.
14 The hydroxyl and amino protected substrate.
16 The hydroxyl deprotected substrate.
18 The phosphate triester formed between 12 and 16, after oxidation.
20 The substrate bound modified form of 18 formed by chemical or enzymic action
22 The product from removal of the Z protecting group from 20.
24 The byproduct formed by expulsion of R*—OH.
26 The product R*—OH.

SUMMARY OF THE INVENTION

The invention is a method which allows the attachment of an alcohol to a substrate by the use of which chemical and/or enzymatic transformations of the alcohol are facilitated, and subsequently the modified alcohol can be released, if desired, under exquisitely mild conditions, after selective removal of a protecting group from an expulsion promoting amino group.

DESCRIPTION OF THE INVENTION

The principle of the invention lies in the observation that an appropriately positioned amino group facilely attacks intramolecular phosphate triesters, and that a subsequent elimination from the resultant complex expels the alcohol, R—OH under mild conditions. Alternative explanations provide other mechanisms to explain the observation.

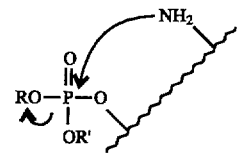

All primary and secondary alcohols can be easily converted to phosphoramidite derivatives (S. L. Beaucage and M. H. Caruthers, Tetrahedron Letters, 1981, 22, 1859). After coupling, the products are rapidly and nearly quantitatively converted to phosphate triester derivatives (18 in this invention).

Structure of 18

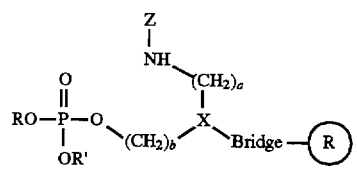

These principles are usefully applied with a suitable substrate (diagramatically represented as a wavy line in the drawing above). This substrate may be a soluble molecule, such as asteroid, polymer or fat whose solubility properties allow ready separation from reagents, or an insoluble material, whereby the immobilized construct is simply separated by filtration centrifugation or decantation, thereby facilitating handling, repeated treatments, and automation.

The crucial amino group is provided with a selectively removable protecting group, Z, separated from the attachment hydroxyl via a framework of atoms, which is also configured to bear a bridging group to attach the linker onto the substrate —(R). It is synthetically convenient to provide the hydroxylic construct 16 with a protecting Group, Y (14), removed prior to attachment of the alcohol.

The application of the method involves the conversion of R—OH (10) to its phosphoramidite derivative (1Z) and coupling to the hydroxylic support (16). As opposed to other methods, amidite derivatives are ideal for this purpose. They are prepared in quantitative yield by the rapid reaction with the corresponding bis(diNR")$_2$ phosphine derivative, and couple, as shown by the work of Beaucage and Caruthers (S. L. Beaucage and M. H. Caruthers, Tetrahedron Letters, 1981, 22, 1859) in v. high yield in less than 2 minutes, typically. The alcohol is attached to the construct as a phosphate triester after oxidation (iodine, peroxide or similar reagent). The stability of the phosphate is dependant on the nature of R'. This is typically selected to be a simple free or substituted hydrocarbon or aromatic residue, which may be removed by concentrated ammonia or strong amine treatment, but is otherwise stable to a range of treatments. If R' is eliminated by such treatments, before removal of Z, then the partially deprotected negatively charged phosphate diester resulting will be highly stable, and R—OH will be permanently immobilized.

The key ability conferred by the method is to chemically or enzymically modify R to R* whilst it is immobilized. It should be noted that the imobilizing phosphate triester bond is stable to most enzymatic, reductive, oxidative or acidolytic chemical reaction conditions. Such modification steps may be extremely simple, such as in the chemical hydroxylation of a double bond within R, or highly complicated, such as in multi-step processes building up specific sequence peptides or oligonucleotides. In such cases R* may bear a plethora of optionally masked functional groups introduced to ensure specificity in the assembly steps. In this actuality it is frequently advantageous to remove these additional groups prior to selective removal of Z, and mild buffer elimination of R*.

Z may be any protecting group stable to the conditions used for R→R* transformations. It may be selected from groups removable by hydrogenation, (e.g. benzyloxycarbonyl), mild acid (e.g. t-butyloxycarbonyl, phenylisopropyloxycarbonyl), mild base (e.g. trifluoroacetyl, fluorenylmethyloxycarbonyl), enzymatic removal (e.g. phenacetyl), oxidation or reduction (e.g. nitrophenylsulphenyl, nitropyridylsulphenyl, dithiasuccinoyl), or by palladium catalyzed transfer to an acceptor (allyloxycarbonyl). In cases where cleavage of R* into solution is required, mild base treatment will eliminate R', and therefore mild base removable protection for Z is incompatible. Groups which require drastic basic conditions for their removal, and which cause phosphate triester deprotection, such as phthaloyl, are specifically excluded.

The construct may be such that —Ⓡ is a soluble substrate, such as a soluble polymer; or may be an insoluble substrate (such as a polystyrene, polyolefin, glass or ceramic derivative).

PREFERRED EMBODIMENTS OF THE INVENTION

The following provides preferred embodiments of the invention; these are provided for the sake of clarity, but are not intended to be restrictive, and it is understood that those qualified or skilled in organic chemistry could readily produced variations which are intended to be covered by the entire scope and spirit of the invention.

Preferred embodiments of the method are provided by the following examples of R, and modifications to produce R*.

When R is a protected ribonucleoside or protected nucleoside derivative, and the attachment hydroxyl is provided by the 2', 3' or 5' hydroxyl of the ribose ring. R may then be subsequently enzymically modified, e.g. by phosphorylation, or chemically, e.g. by repetitive chemical treatments performing assembly of nucelotide sequences of known sequence. The substrate is preferably polyethylene glycol, silica, controlled pore glass, membranes, polyolefin, or polystyrene or polyethyleneglycol-polystyrene graft copolymers.

When R is a protected derivative of serine, threonine, hydroxyproline or tyrosine, and these amino acid derivatives are subsequently chemically or enzymically modified to provide determined sequence peptides.

When R is a suitable scaffold containing multiple alternative protecting groups for the construction of a library of derivatives of the scaffold by the principles of combinatorial chemistry (reviewed by inventor). In this case, the ability of the invention to permit cleavage of the multitudinous products under aquous conditions directly into assay media is of exceptional importance.

A further preferred embodiment of the invention is where the bridging atoms, $(CH_2)_a$—X—$(CH_2)_b$, are derived from 3-amino-1,2-propanediol. The structures of these specific forms of 14 and 18 are given below.

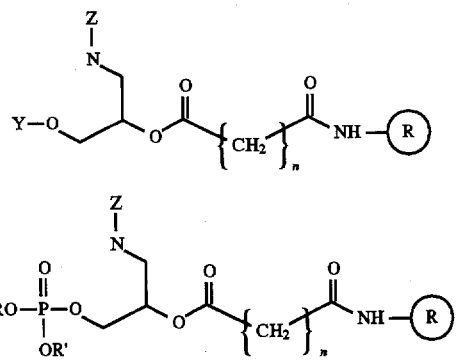

The Z protected adduct is functionalized at the 2-hydroxyl by reaction with a dicarboxylic acid, thereby providing an easy means to attach the APEX linker to any amino functionalized substrate.

Further preferred embodiments of the invention is provided when Z is selected as allyloxycarbonyl (Aloc-), and Y is selected as dimethoxytrityl (DMT-). The allyloxycarbonyl group has been used for both the side-chain protection of nucleoside residues in DNA and RNA synthesis (Y. Hayakawa, S. Wakabayashi, H. Karo aand R. Noyori, *J. Amer. Chem. Soc.*, 1990, 112, 1691), as well as for peptide sythesis (D. Hudson and M. H. Lyttle, in Peptides, Chemistry and Biology, Proceedings of the Twelfth American Peptide Society, J. Rivier and J. A. Smith, Eds, Escom, Leiden, 1992, p.583, A. Loffet and H. Zhang, World Patent, WO 92/19643). The Aloc group is stable to most acidic and basic reaction conditions, and is removed mildly and specifically by Pd(0) catalysed transfer to a suitable acceptor (e.g. an amine or amine salt). The DMT- group is removed rapidly by very mild acid such that any selection for Z remains unmodified.

The following examples give details of the preparation of APEX linkers, and of the application of the method.

EXAMPLE 1

Synthesis of 1-O-(4,4'dimethoxytrityl)-2-O-succinoyl-3-N-allyloxycarbonyl propane 10 g of 3-amino-1,2-propane diol was dissolved in a mixture of 200 mL of water and 50 mL of THF. To this was added 10 g $K_2CO_3$, followed by dropwise addition, over 30 min, of 30 mL allyl chloroformate 3 in 100 mL of THF. The reaction was stirred for 2 hrs, with more $K_2CO_3$ added, as needed, to maintain a pH of 9–10. The mixture was cautiously acidified to pH 4 with dilute HCl, and extracted twice with 200 mL EtOAc. The combined organic layers were dried over $Na_2SO_4$ and concentrated to 8 g (42% yield) of a clear oil. The oil was negative to a ninhydrin test whereas the starting material was strongly positive. 1H NMR, 360 mHz, $CDCl_3$, d: 3.2 (dt, 1H), 3.3 (dt, 1H), 3.5 (dd, 1H), 3.6 (dd, 1H), 3.75 (m, 1H), 3.9 (broad s, 2H), 4.5(d, 2H), 5.2(dd, 2H), 5.3(dd, 2H), 5.9(m, 2H).

The total of this product (45.7 mM) was dissolved in 100 mL of pyridine and reduced to an oil in vacuo. The oil was dissolved in 200 mL of pyridine, and 18 g (53 mM) of 4,4'dimethoxytrityl chloride was added. The red mixture was stirred overnight. 20 mL of methanol was added to the mixture, and the solvent was removed in vacuo after 20 min. The residue was dissolved in 300 mL of EtOAc, and the organic phase was washed with water, 200 mL, and dried over $MgSO_4$. The solution was filtered and reduced to a tar in vacuo A 4×40 cM silica column was prepared in $CH_2Cl_2$ with 1% v:v pyridine. The crude product was loaded onto the column and eluted with 1 L of this solvent, followed by 1 L of 1% MeOH/$CH_2Cl_2$, then 1 L of 2% MeOH/$CH_2Cl_2$. 500 mL fractions were collected, and those which contained pure product, r.f. 0.73 (5% MeOH/$CH_2Cl_2$, aluminum backed silica plates) were pooled to give 7.4 g (31.5% yield) of an orange oil. $^1$H NMR, 360 mHz, $CDCl_3$, d: 3.2(m, 3H), 3.4(m, 1H), 3.8(s, 6H), 3.9(m, 1H), 4.6(d, 2H), 5.6(broad s, 1H) , 5.7 (dd, 1H), 5.8(dq, 1H), 5.9(dq, 1H), 6.8(s, 1H), 6.9(m, 4H), 7.2(m, 1H), 7.3(m, 6H), 7.4(d, 2H).

5 g ( 10 mM) was dissolved in 100 mL of pyridine and reduced to an oil in vacuo. The oil was dissolved in 200 mL of pyridine, and 10 g (100 mM) of succinic anhydride was added, along with 1 mL of n-methyl imidazole. The mixture was allowed to stand overnight, after the solids were dissolved by swirling the flask. Methanol, 20 mL, was added, and the solvents were removed in vacuo A 4×40 cM silica column was prepared in $CH_2Cl_2$ with 1% v:v triethylamine. The crude product was loaded onto the column and eluted with 1 L of this solvent, followed by 2 L of 1% MeOH/$CH_2Cl_2$, then 1 L of 4% MeOH/$CH_2Cl_2$, then 1 L of 6% MeOH/$CH_2Cl_2$. 500 mL fractions were collected, and those which contained pure product, r.f. 0.27 (5% MeOH/$CH_2Cl_2$, aluminum backed silica plates) were pooled to give 5 g (84% yield, orange oil) of the desired product as its triethylammonium salt. $^1$H NMR, 360 mHz, $CDCl_3$, d: 1.25(t, 9H), 2.6(m, 4H), 3.1(q, 6H), 3.2(d, 2H), 3.3(m, 1H), 3.5(m, 1H), 3.8(s, 6H), 4.5(d, 2H), 5.0–5.3(m, 3H), 5.9(dq, 1H), 6.9(d, 4H), 7.2(dd, 1H), 7.3(m, 7H), 7.4(d, 2H), 8.6(d, 1H).

EXAMPLE 2

Immobilization of 1-O-(4,4'dimethoxytrityl)-2-O-succinoyl-3-N-allyloxycarbonyl propane on Controlled Pore Glass (CPG)

In a 125 mL erlenmyer flask, 1 g (1.6 mM) of the linker was dissolved in 22 mL of DMF. 150 mg of hydroxybenzotriazole (HOBT) was added, and the mixture was swirled until this dissolved. Next 0.2 mL of diisopropylcarbodiimide (DIPCDI) was added, followed immediately by 10 g of aminopropyl 1000 A CPG. The mixture was allowed to stand overnight, whereupon preliminary testing of the loading gave 12 mM/g. Another g of 1 and 0.2 mL more DIPCDI were added, and the mixture was again allowed to stand overnight. The support was washed with two 100 mL portions of acetonitrile, and then excess amino groups on the support were acetylated with 100 mL of a mixture of 5:5:8:82 $Ac_2O$:pyridine:n-methylimidazole:THF for 1 hr. The support was then rinsed with two 100 mL washes of acetonitrile, two 100 mL washes of MeOH and two 100 mL washes of $CH_2Cl_2$. After overnight drying in vacuo the loading was 17 mM/g.

EXAMPLE 3

DNA synthesis with automated introduction of 3'terminal residue

The following 4 nucleotides were prepared with automated incorporation of all 4 of the bases as their 3' terminal nucleotide phosphoramidites:
CGATCTGAATAGCTT, ATACTTATCATGAGCC, TCCACGTCATCGAGGTCATA, GATGAGTCCGTGTCCGTACAACTGG.

All couplings were performed with standard protocols on a Biosearch Model 8700 DNA synthesizer using di(iso) propyl-β-cyanoethyl phosphoramidite derivatives of the nuceolitide bases both for 3' terminal attachment to the linker functionalized support of example 2, and for all subsequent chain elongation steps. Coupling efficiencies were monitored spectrophotometrically and were in the range 97.5 to 99%.

EXAMPLE 4

Deprotection of the APEX linker and cleavage of DNA from the Universal Support

The automated DNA syntheses of the above examples were concluded with the 5'-DMT group removed. A mixture of 25 mg tetrakistriphenylphosphine palladium(0), 50 mg of ammonium acetate hydrate and 100 mg of triphenyl phosphine in 1 mL of THF was heated to 50° C. for 2 min. 200 μL of the yellow solution was taken up in a 1 mL syringe and about 1/2 of this was passed into the DNA synthesis column containing the support bound nucleotide. The column, with syringe attached was placed in a previously warmed 13×100 mm test tube and heated in an aluminum hot block at 50° C. After 10 min, the rest of the solution was forced through the column, and after 5 min the column was removed from the tube and washed with 5 mL acetonitrile on the DNA synthesizer. Next, a solution of 1 mL 0.1N triethylamine acetate (TEAA), pH 8.5, was mixed with 40 mL of 3% aqueous ammonia, and 0.5 mL of this solution was taken up in a syringe. Over 2 hrs, this solution is pushed through the column in small increments, with the effluent collected in an eppendorf tube. The column was then further rinsed with 0.5 mL 50% acetonitrile in water, and the combined effluent evaporated in vacuo The residue was then subjected to concentrated ammonia for 5 hrs at 55°, and evaporated for subsequent purification or analysis.

The 4 oligonucleotide products were shown to be identical to DNA synthesized using standard DMT-dA(Bz)-succ-Ap-CPG, DMT-dC(Bz)-Ap-CPG, DMT-dG(iBu)-succ-AP-CPG and DMT-T-succ-Ap-CPG. Comparisons were made by polycrylaide gel electrophoresis, ion-exchange and reverse phase HPLC, and by mass spectrometry. In addition the 25 mer sequence is a PCR primer, and was shown to amplify DNA as efficiently as authentic product supplied in the PE/ABI PCR kit.

We claim:

1. A method for the immobilization and subsequent release of an organic hydroxylic compound, R—OH, comprising the following steps:

i) converting the molecule R—OH into its phosphoramidite derivative R—O—P(OR')—N(R")$_2$ wherein R is a primary, secondary, or tertiary aliphatic or aromatic group which may or may not contain other functional groups;

wherein R' is selected from the group consisting of methyl, ethyl, cyanoethyl, phenyl, chlorophenyl, and other aliphatic, branched aliphatic or aromatic groups;

wherein R" is selected from the group consisting of methyl, ethyl, isopropyl and other linear and branched aliphatic groups;

ii) a hydroxyl protecting group Y is selectively removed from a derivatized solid support having the structure

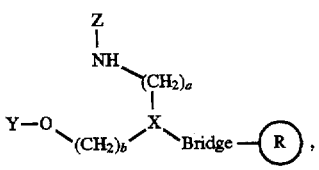

where a+b is greater than 1 but less than 6, and X is a nitrogen or CH group, wherein said structure is attached to a solid support —(R) by a bridge group selected from the group consisting of bifunctional aliphatic, bifunctional branched aliphatic, bifunctional polyethylene glycol containing and bifunctional aromatic groups;

iii) said phosphoramidite is attached to said hydroxyl deprotected derivatized solid support by activation with a tetrazole solution or other phosphoramidite activator solution, followed by oxidation of the phosphorus with iodine solution or other oxidant solution to produce a compound having the structure

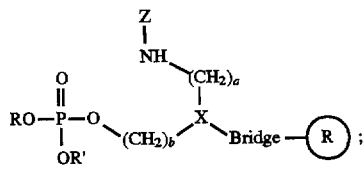

iv) the protecting group Z of the intermediate produced by step iii which masks the nitrogen functionality is removed selectively, and;

v) the intermediate produced by step iv is contacted with a mildly basic buffer solution to promote intramolecular attack at phosphorus by the nitrogen to produce the compound R—OH.

2. The method of claim 1 wherein a is 1 and b is 1.

3. The method of claim 1 wherein the framework of atoms $(CH_2)_b$—X—$(CH_2)_a$ is attached to a dicarboxylic acid via an ester or amide bond to X, and wherein —(R) is an amino functionalized surface or particle to which the other end of the dicarboxylic acid is attached via an amide bond.

4. The method of claim 1 wherein Z is a protecting group selected from the group consisting of t-butyloxycarbonyl, dithiasuccinoyl, nitrobenzyloxycarbonyl and allyloxycarbonyl.

5. The method of claim 1 further comprising chemical or enzymatic modification of the alcohol R—OH carried out between the steps of immobilization and release of the compound R—OH.

6. The method of claim 1 wherein Z is allyloxycarbonyl, and Z is removed by a THF solution of tetrakistriphenylphosphine palladium (0), ammonium acetate and triphenylphosphine.

7. The method of claim 1 wherein R—OH is a nucleoside or ribonucleoside derivative, derivatized as a phosphoramidite at any one of positions 5', 3' or 2'.

8. The method of claim 1 wherein —(R) is selected from the group consisting of controlled pore glass, microporous polyolefin, plasma aminated membrane, macroreticular polystyrene, polyhydroxymethacrylate and polyethyleneglycol-polystyrene graft copolymer.

9. The method of claim 1 wherein the bridge group is attached to the solid support —(R) and X of the framework of atoms $(CH_2)_b$—X—$(CH_2)_a$ by functional groups selected from the group consisting of amide, ester, ether, phosphate, urethane, urea and amine.

10. The method of claim 1 wherein Y is a protecting group selected from the group consisting of 4,4'-dimethoxytrityl 4-methoxytrityl, trityl and other acid labile protecting groups.

11. The method of claim 1 wherein Y is a hydrogen.

12. A method for the release of an organic hydroxylic compound R—OH from a solid support having the structure

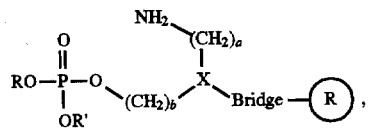

where a+b is greater than 1 but less than 6, and X is a nitrogen or CH group;

wherein said structure is attached to a solid support —(R) by a bridge group selected from the group consisting of bifunctional aliphatic, bifunctional branched aliphatic, bifunctional polyethylene glycol containing and bifunctional aromatic groups between X and the support —(R);

wherein R is a primary, secondary, or tertiary aliphatic or aromatic group which may or may not contain other functional groups;

wherein R' is selected from the group consisting of methyl, ethyl, cyanoethyl, phenyl, chlorophenyl, and other aliphatic, branched aliphatic and aromatic groups comprising contacting said structure with a mildly basic buffer solution to promote intramolecular attack at phosphorus by the nitrogen to produce the compound R—OH.

13. The method of claim 12 wherein R—OH is an oligodeoxyribonucleotide, oligoribonucleotide, peptide, or oligonucleotide-peptide conjugate.

14. The method of claim 12 wherein —(R) is selected from the group consisting of controlled pore glass, microporous polyolefin, plasma aminated membrane, polystyrene, macroreticular polystyrene, polyhydroxymethacrylate and polyethyleneglycol-polystyrene graft copolymer.

15. The method of claim 12 wherein the bridge group is attached to the solid support —(R) and X of the framework of atoms $(CH_2)_b$—X—$(CH_2)_a$ by functional groups selected from the group consisting of amide, ester, ether, phosphate, urethane, urea and amine.

* * * * *

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
( A ) LENGTH: 15 Bases

-continued ( B ) TYPE: nucleic acid
                    ( C ) STRANDEDNESS: single
                    ( D ) TOPOLOGY: linear ( i i ) MOLECULE TYPE: synthetic DNA ( i i i ) HYPOTHETICAL: no ( i v ) ANTI-SENSE: no ( v i ) ORIGINAL SOURCE:
                    ( A ) ORGANISM:
                    ( C ) INDIVIDUAL ISOLATE:
                    ( G ) CELL TYPE:

( v i i ) IMMEDIATE SOURCE:
                    ( A ) LIBRARY:
                    ( B ) CLONE:

( x ) PUBLICATION INFORMATION:
                    ( A ) AUTHORS: Lyttle, Matthew H., Hudson, Derek. Cook, Ron M.
                    ( B ) TITLE: A New Universal Linker for solid phase DNA Synthesis
                    ( C ) JOURNAL: Nucleic Acids Research
                    ( D ) VOLUME: 24
                    ( E ) ISSUE: 14
                    ( F ) PAGES: 2793 - 2798
                    ( G ) DATE: July 15, 1996
                    ( K ) RELEVANT RESIDUES IN SEQ ID NO: 1: FROM 1 TO 15

( x i ) SEQUENCE DESCRIPTION: SEQ ID NO: 1:

CGATCTGAAT    AGCTT                                                                                 15

( 2 ) INFORMATION FOR SEQ ID NO: 2:

( i ) SEQUENCE CHARACTERISTICS:
                    ( A ) LENGTH: 16 Bases
                    ( B ) TYPE: nucleic acid
                    ( C ) STRANDEDNESS: single
                    ( D ) TOPOLOGY: linear ( i i ) MOLECULE TYPE: synthetic DNA ( i i i ) HYPOTHETICAL: no ( i v ) ANTI-SENSE: no ( v ) ORIGINAL SOURCE:
                    ( A ) ORGANISM:
                    ( C ) INDIVIDUAL ISOLATE:
                    ( G ) CELL TYPE:

( v i ) IMMEDIATE SOURCE:
                    ( A ) LIBRARY:
                    ( B ) CLONE:

( x ) PUBLICATION INFORMATION:
                    ( A ) AUTHORS: Lyttle, Matthew H., Hudson, Derek. Cook, Ron M.
                    ( B ) TITLE: A New Universal Linker for solid phase DNA Synthesis
                    ( C ) JOURNAL: Nucleic Acids Research
                    ( D ) VOLUME: 24
                    ( E ) ISSUE: 14
                    ( F ) PAGES: 2793 - 2798
                    ( G ) DATE: July 15, 1996
                    ( K ) RELEVANT RESIDUES IN SEQ ID NO: 2: FROM 1 TO 16

( x i ) SEQUENCE DESCRIPTION: SEQ ID NO: 2:

ATACTTATCA    TGAGCC                                                                                16

( 2 ) INFORMATION FOR SEQ ID NO: 3:

( i ) SEQUENCE CHARACTERISTICS:
                    ( A ) LENGTH: 20 Bases
                    ( B ) TYPE: nucleic acid
                    ( C ) STRANDEDNESS: single
                    ( D ) TOPOLOGY: linear -continued (ii) MOLECULE TYPE: synthetic DNA (iii) HYPOTHETICAL: no (iv) ANTI-SENSE: no (v) ORIGINAL SOURCE:
 (A) ORGANISM:
 (C) INDIVIDUAL ISOLATE:
 (G) CELL TYPE:

(vi) IMMEDIATE SOURCE:
 (A) LIBRARY:
 (B) CLONE:

(x) PUBLICATION INFORMATION:
 (A) AUTHORS: Lyttle, Matthew H., Hudson, Derek. Cook, Ron M.
 (B) TITLE: A New Universal Linker for solid phase DNA Synthesis
 (C) JOURNAL: Nucleic Acids Research
 (D) VOLUME: 24
 (E) ISSUE: 14
 (F) PAGES: 2793 - 2798
 (G) DATE: July 15, 1996
 (H) RELEVANT RESIDUES IN SEQ ID NO: 3: FROM 1 TO 20

(xi) SEQUENCE DESCRIPTION: SEQ ID NO: 3:

TCCACGTCAT CGAGGTCATA 20

(2) INFORMATION FOR SEQ ID NO: 4:

(i) SEQUENCE CHARACTERISTICS:
 (A) LENGTH: 25 Bases
 (B) TYPE: nucleic acid
 (C) STRANDEDNESS: single
 (D) TOPOLOGY: linear (ii) MOLECULE TYPE: synthetic DNA (iii) HYPOTHETICAL: no (iv) ANTI-SENSE: no (v) ORIGINAL SOURCE:
 (A) ORGANISM:
 (C) INDIVIDUAL ISOLATE:
 (G) CELL TYPE:

(vi) IMMEDIATE SOURCE:
 (A) LIBRARY:
 (B) CLONE:

(x) PUBLICATION INFORMATION:
 (A) AUTHORS: Lyttle, Matthew H., Hudson, Derek. Cook, Ron M.
 (B) TITLE: A New Universal Linker for solid phase DNA Synthesis
 (C) JOURNAL: Nucleic Acids Research
 (D) VOLUME: 24
 (E) ISSUE: 14
 (F) PAGES: 2793 - 2798
 (G) DATE: July 15, 1996
 (K) RELEVANT RESIDUES IN SEQ ID NO: 4: FROM 1 TO 25

(xi) SEQUENCE DESCRIPTION: SEQ ID NO: 4:

GATGAGTCCG TGTCCGTACA ACTGG 25